(12) United States Patent
Fransson et al.

(10) Patent No.: US 8,544,682 B2
(45) Date of Patent: Oct. 1, 2013

(54) METHOD AND DEVICE FOR THE SERIAL EJECTION OF TWO FLUIDS COMPRISING A SPACER

(75) Inventors: Jonas Fransson, Uppsala (SE); Birger Hjertman, Hässelby (SE)

(73) Assignee: Swedish Orphan Biovitrum AB, Stockholm (SE)

( * ) Notice: Subject to any disclaimer, the term of this patent is extended or adjusted under 35 U.S.C. 154(b) by 341 days.

(21) Appl. No.: 12/743,683

(22) PCT Filed: Nov. 21, 2008

(86) PCT No.: PCT/SE2008/051336
§ 371 (c)(1),
(2), (4) Date: Sep. 2, 2010

(87) PCT Pub. No.: WO2009/067082
PCT Pub. Date: May 28, 2009

(65) Prior Publication Data
US 2010/0327007 A1 Dec. 30, 2010

(30) Foreign Application Priority Data
Nov. 22, 2007 (SE) ...................... 0702574

(51) Int. Cl.
*B67D 7/70* (2010.01)
*A61M 37/00* (2006.01)
*B67B 7/00* (2006.01)
*G01F 11/00* (2006.01)

(52) U.S. Cl.
USPC ....... 222/1; 604/82; 604/89; 604/90; 222/135

(58) Field of Classification Search
USPC ................... 222/129, 135, 145.1, 145.5, 386; 206/219; 604/82–85, 89–91, 191, 263
See application file for complete search history.

(56) References Cited

U.S. PATENT DOCUMENTS

| 3,380,451 | A | * | 4/1968 | Porter et al. ................... 604/90 |
| 4,235,235 | A | * | 11/1980 | Bekkering ..................... 604/238 |
| 4,439,184 | A | | 3/1984 | Wheeler |
| 4,529,403 | A | * | 7/1985 | Kamstra ........................ 604/136 |
| 4,573,972 | A | * | 3/1986 | Kamstra ........................ 604/191 |
| 4,668,223 | A | * | 5/1987 | Grotenhuis ..................... 604/191 |

(Continued)

FOREIGN PATENT DOCUMENTS

| EP | 0721357 B1 | 3/2002 |
| WO | WO 9401150 | 1/1994 |
| WO | WO 0162319 | 8/2001 |
| WO | WO 2006118949 | 11/2006 |

OTHER PUBLICATIONS

International Search Report and Written Opinion for PCT/SE2008/051336, Feb. 25, 2009.

*Primary Examiner* — Paul R Durand
*Assistant Examiner* — Vishal Pancholi
(74) *Attorney, Agent, or Firm* — Fish & Richardson P.C.

(57) ABSTRACT

A device for the serial ejection of at least two fluid components comprises a spacer (19) providing at least two states, i) a first state allowing a front piston (7) to be displaced forwards by action on a rear piston (17) while a fluid volume is retained in a rear chamber (5) and ii) a second state allowing the rear chamber to volumetrically shrink while fluid is transferred past (or through) the front piston thereby enabling the use of a liquid, initially provided in only the rear chamber, for the dual purposes of mixing and rinsing.

25 Claims, 3 Drawing Sheets

(56) References Cited

U.S. PATENT DOCUMENTS

| | | | | |
|---|---|---|---|---|
| 4,792,329 A | * | 12/1988 | Schreuder | 604/90 |
| 4,820,286 A | * | 4/1989 | van der Wal | 604/89 |
| 4,822,340 A | * | 4/1989 | Kamstra | 604/135 |
| 4,968,299 A | * | 11/1990 | Ahlstrand et al. | 604/90 |
| 5,080,649 A | * | 1/1992 | Vetter | 604/91 |
| 5,253,785 A | * | 10/1993 | Haber et al. | 222/43 |
| 5,549,561 A | * | 8/1996 | Hjertman | 604/131 |
| 5,549,574 A | * | 8/1996 | Townsend | 604/232 |
| 5,716,338 A | * | 2/1998 | Hjertman et al. | 604/89 |
| 5,830,193 A | * | 11/1998 | Higashikawa | 604/191 |
| 5,899,881 A | * | 5/1999 | Grimard et al. | 604/89 |
| 6,228,065 B1 | * | 5/2001 | Lynn | 604/191 |
| 6,544,233 B1 | * | 4/2003 | Fukui et al. | 604/191 |
| 6,723,074 B1 | * | 4/2004 | Halseth | 604/201 |
| 6,740,062 B2 | * | 5/2004 | Hjertman | 604/187 |
| 6,817,987 B2 | * | 11/2004 | Vetter et al. | 604/85 |
| 6,893,420 B2 | * | 5/2005 | Arnisolle | 604/135 |
| 6,997,910 B2 | * | 2/2006 | Howlett et al. | 604/191 |
| 2002/0045865 A1 | * | 4/2002 | Mitomi et al. | 604/207 |
| 2002/0183690 A1 | * | 12/2002 | Arnisolle | 604/83 |
| 2004/0097875 A1 | * | 5/2004 | Bae | 604/89 |
| 2006/0184118 A1 | * | 8/2006 | Hjertman | 604/141 |

\* cited by examiner

METHOD AND DEVICE FOR THE SERIAL EJECTION OF TWO FLUIDS COMPRISING A SPACER

CROSS REFERENCE TO RELATED APPLICATIONS

This application is a national phase filing under 35 U.S.C. §371 of International application number PCT/SE2008/051336, filed Nov. 21, 2008, which claims priority from Swedish application number 0702574-5, filed Nov. 22, 2007. The entire content of the prior applications are incorporated herein by reference in their entirety.

FIELD OF THE INVENTION

The present invention relates to a device for serial ejection of at least two fluid components, such as an injection cartridge. The invention further relates to methods for manufacturing such devices, methods for ejecting at least two components from such devices and the use of such devices for mixing and rinsing.

BACKGROUND OF THE INVENTION

Injection cartridges have found a wide use for administering injectable pharmaceutical preparations by means of injection or infusion. Such cartridges have a number of important advantages over the use of syringes filled before use from a separate vial, such as their ease of handling and the lessened risk of microbial contamination. An injection cartridge generally comprises a tubular barrel, which contains a liquid injectable preparation. At its front end, the barrel is sealed by a closure, which may be pierced by an outlet conduit, such as an injection needle or cannula or a tube for infusion. At its rear end, the cartridge is closed by a piston, which may be moved forward to expel the injectable preparation from the cartridge through the outlet conduit. This type of injection cartridge is known as a single-chamber injection cartridge.

Dual-chamber injection cartridges are also well-known. Such cartridges are intended to be used for injectable preparations which are not stable in their ready-to-use state, and the space between the front closure and the rear piston is divided into two chambers, which are separated by a separating movable wall. The front chamber usually contains a solid component of the injectable preparation, and the rear chamber contains a liquid component of said preparation. At a predetermined position in the cartridge, there is arranged a longitudinally extending liquid bypass arrangement in the wall of the cartridge, such that the liquid component may bypass the movable separating wall and flow into the front chamber to be mixed with the solid component. When a forwardly directed pressure is applied to the rear piston, this pressure will be translated through the liquid to urge the movable wall forward. When the movable wall has moved far enough towards the front chamber such that the inlet of the bypass arrangement is open to the rear chamber, further forward movement of the rear piston will cause the liquid from the rear chamber to flow through said bypass arrangement and mix with the component in the front chamber. In this way, the two components may be mixed with each other just before the injection is to be administered, and there will be no time for degradation of the ready-mixed preparation. Once all the liquid has been transferred from the rear chamber to the front chamber, further movement of the rear piston will cause it to abut the movable separating wall, and with continued movement forward rear piston and movable separating wall will act as a single piston for expelling the mixed preparation from the cartridge.

U.S. Pat. No. 4,439,184 discloses a two-dose syringe with a dual chamber, intended to provide two separate bodies of fluid in a sequence. As a first body of fluid is pushed out of the syringe a first piston, made of resilient material, reaches a bypass zone having at least one ridge projecting into the fluid chamber from its wall. This ridge pushes the first piston away from the wall so that the fluid between the first and second pistons can pass around the first piston to an output zone.

A dual-chamber injection cartridge is disclosed in WO 94/01150. It has a front chamber for a solid component and a rear chamber for a liquid component. The injection cartridge further comprises a bypass constriction with a non-circular cross-section for allowing the flow of liquid from the rear chamber into the front chamber when a front piston of resilient material is urged into the constriction by the movement of a rear piston.

As indicated, known in the art are multiple chamber cartridges comprising a) a barrel having a front face comprising an outlet (or preparation for an outlet), b) a movable front piston in the barrel which defines a front chamber between the front piston and the front face of the barrel c) a movable rear piston defining a rear chamber between the rear piston and the front piston d) a rear bypass allowing fluid transfer from the rear chamber to the front chamber and e) a front bypass allowing fluid transfer past (or through) the front piston to the outlet.

Antihaemophilic preparations are normally stored and distributed in lyophilized form, reconstituted before administration and injected via a needle or tube with cannula. When the administration of a liquid preparation from an injection cartridge has been finished and the rear piston is in its foremost position, there exists a dead volume of unusable preparation in front of the piston in the front end part of the cartridge and in the outlet of the cartridge. This dead volume can be considerable, especially when a tube of some length is arranged between the outlet and the needle or cannula. This is a disadvantage, as it means that a certain amount of the pharmaceutical preparation will not be utilized by the patient. The disadvantage is aggravated when very expensive pharmaceutical preparations are used, such as growth hormones and certain peptides.

Various ways have been tried to eliminate this disadvantage. One way has been to draw some blood back into the cartridge after the finished injection and then inject it back into the patient, so that the outlet is rinsed in this way. This practice, however, is not to be recommended, as there is a risk that the components of the blood, which are very sensitive to surfaces, will be destroyed or will coagulate to form clots. Another way has been to remove the syringe containing the pharmaceutical agent and replace it with a syringe containing a rinsing liquid, such as physiological saline solution, to finish the injection. This is complicated and time-consuming, and increases the risk of spillage and contamination.

There are known cartridges having a third chamber which is arranged to allow for both mixing of two components into a mixture before ejection, as well as ejection of a rinsing liquid following the ejection of the mixture, resulting in a two-step sequential ejection pattern.

EP 0 721 357 discloses a three-chamber injection cartridge containing a front chamber with a solid preparation component, an intermediate chamber with a liquid component, a rear chamber with a rinsing liquid and rear and front bypasses for reconstitution and sequential ejection respectively. This injection cartridge could offer a solution to the disadvantage of dead volumes when administering pharmaceutical preparations. There are however very few manufacturing plants in the world that manufacture injection cartridges pre-filled with lyophilized products and all of these lack process stations for charging a third chamber and a third piston. Hence there is a need for a user-friendly and efficient injection cartridge enabling the full use of valuable pharmaceutical preparations.

SUMMARY OF THE INVENTION

The present invention removes at least some of the disadvantages of prior art injection cartridges by providing a two-chamber device, such as an injection cartridge, for administration of injections or infusions.

In a first aspect of the invention there is provided a two-chamber device supplied with a spacer providing at least two states, i) a first state allowing the front piston to be displaced forwards by action on the rear piston while a fluid volume is retained in the rear chamber and ii) a second state allowing the rear chamber to volumetrically shrink while fluid is transferred past (or through) the front piston thereby enabling the use of a liquid, initially provided in only the rear chamber, for the dual purposes of mixing and rinsing.

In a second aspect the invention provides said two-chamber device comprising a first component in the front chamber being a solid, liquid or lyophilized substance and a liquid component in the rear chamber acting as both reconstitution liquid and rinsing liquid.

In another aspect of the invention there is provided a method for manufacturing said two-chamber device in a way that renders it possible to utilize already existing manufacturing plants.

In yet another aspect of the invention there is provided a method for ejecting a liquid preparation and a rinsing liquid from said two-chamber device.

In still another aspect of the invention there is provided the use of said two-chamber device for performing injections or infusions.

DETAILED DESCRIPTION OF THE INVENTION

The present invention relates to a device for the serial ejection of at least two fluid components comprising a) a barrel, having a longitudinal axis, having a front end face or side portion with an outlet, or preparation for an outlet, b) a movable front piston in the barrel defining a front chamber between the front piston and the barrel front, c) a movable rear piston defining a rear chamber between the rear piston and the front piston, d) a rear bypass arrangement allowing fluid transfer from the rear chamber to the front chamber and e) a front bypass arrangement allowing fluid transfer past (or through) the front piston to the outlet, wherein a spacer provides at least two states, i) a first state allowing the front piston to be displaced forwards by action on the rear piston while a fluid volume is retained in the rear chamber and ii) a second state allowing the rear chamber to volumetrically shrink while fluid is transferred past (or through) the front piston.

There are a plurality of different mechanisms available for allowing a spacer to change from a first state allowing the front piston to be displaced forwards by action on the rear piston while a fluid volume is retained in the rear chamber to a second state allowing the rear chamber to volumetrically shrink while fluid is transferred past (or through) the front piston. These include: the spacer changing length by collapsing, the spacer changing volume by collapsing, crushing or bursting or the like, and the spacer penetrating into, and/or being penetrated by another element of the device. In one preferred embodiment of a spacer for providing a first state and a second state, the spacer comprises contact surfaces longitudinally separated by collapsible posts. In another preferred embodiment the spacer comprises penetrating means such as knives for penetrating one or both of said pistons. In still another preferred embodiment the spacer is a collapsible pin projecting from the surface of one piston and facing towards the other piston. In yet another embodiment the spacer is a crushable hollow cushion, which cushion can be part of one piston or a separate component positioned between front and rear pistons. In a further embodiment the spacer comprises a two or more different mechanisms for providing a first state and a second state.

The present invention further relates to a two-chamber device which has its front chamber at least partly filled with a first component that is to be reconstituted or dissolved or suspended by, or mixed with a first portion of a volume of liquid which is initially located in the rear chamber and which is displaced into the front chamber, and subsequently rinsed out by the remaining portion of the liquid located in the rear chamber.

In one preferred embodiment the two-chamber device comprises a solid or lyophilized component located in the front chamber and a liquid initially located in the rear chamber which can act firstly as a reconstitution liquid and secondly as a rinsing liquid.

In another preferred embodiment the device according to the invention comprises a liquid component located in the front chamber and a liquid initially located in the rear chamber which can act firstly as dissolving and/or suspending and/or mixing liquid and secondly as a rinsing liquid.

According to the present invention both mixing prior to ejection from the first chamber as well as rinsing after mixture ejection can be achieved in a two-chamber device if a first portion of the fluid, normally a liquid, in the rear chamber can be used for the mixing purpose and a second portion of the fluid used subsequently for the rinsing purpose. This is made possible by use of a spacer providing at least two states, i) a first state allowing the front piston to be displaced forwards by action on the rear piston while a fluid volume is retained in the rear chamber and ii) a second state allowing the rear chamber to decrease in volume as fluid transfers past (or through) the front piston. The main purpose of the spacer first state is to displace the front piston away from the rear bypass arrangement after which the retained fluid volume in the rear chamber is securely enclosed, with or without the spacer. The displacement of the front piston can take place by mechanical action, e.g. by a spacer bridging a gap between the front piston and the rear piston, or hydraulic action, e.g. by a spacer closing the bypass arrangement, thereby allowing the fluid between the pistons to move the front piston. The main purpose of the spacer second state is to allow the rear chamber to volumetrically shrink, similar to the situation when a spacer is not present, by transferring fluid past (or through) the front piston via the front bypass arrangement to the outlet. However, it is conceivable that the spacer also can be active in this state, for example by assisting in opening the front bypass arrangement, either by mechanical action, e.g. by directly affecting a valve component, or by hydraulic action, e.g. by itself acting as a pressure-sensitive valve. A spacer zero state, preceding the first state, is assumed in which zero state the spacer allows the device to act as a common two-chamber device for mixing, meaning that it allows the rear bypass arrangement to open or be open, e.g. by moving the front piston into the rear bypass zone (i.e. the position where the fluid in the rear chamber can flow through the rear bypass arrangement and therefore the fluid pressure exerted on the front piston during movement of the rear piston is not enough to cause further movement of the front piston), which allows the fluid volume intended for mixing to be transferred from the rear chamber to the front chamber. As mentioned above with respect to the second state, the spacer can be inactive in the zero state, or it can be active and open the rear bypass arrangement by mechanical or hydraulic action.

The front "outlet" shall be understood to mean an opening or preparations for an opening. Pre-filled cartridges normally have a front or side outlet which is sealed for the purpose of preserving and protecting the cartridge content. The outlet is normally prepared for being opened when the device is to be used, e.g. by being provided with a removable cap or penetrable membrane or septum to which can be connected a needle or tube with cannula or needle, forming part of the dead spaces to be rinsed during the final step of injection of the contents.

"Piston" shall be understood to incorporate any form of movable wall including displaceable and extendable membranes although it is preferred to use a common plug-type piston which is movable along the barrel and which elastically seals against the barrel inner surface. Plug type pistons can have valve arrangements allowing controlled fluid transfer through the pistons but it is preferred to use fluid tight plugs of composite, but preferably monolithic, type.

"Zone" shall be understood to mean the region in the vicinity of structures which region may be longer than the structure itself in which piston deformation may occur to such an extent that the passage of fluid past the piston may occur.

The rear bypass arrangement shall be designed to allow to be opened for transfer of at least part of the fluid from the rear chamber past (or through) the piston to the front chamber and preferably also to assist in preventing backflow in the reverse direction. For these purposes the rear bypass can take a variety of forms. Bypasses in the form of valves, i.e. having in themselves means for providing open and closed states, can be used and preferably these are one-way valves, preferably oriented for the desired forward flow direction. As indicated above pistons can be provided with valves that can act as a bypass. For safety against leakage and simplicity it is preferred, however, to use bypass designs connected to or preferably integral with the barrel and preferably the common type in which barrel structures cooperate with the piston for opening and closing the passage past the piston. For example a barrel bypass section may interact with the piston to create leakage past the piston, either by using a longitudinal protuberance extending radially into the interior of the barrel thereby distorting the piston as it passes the bypass and allowing leakage past the piston, or preferably, by being formed as a duct extending externally in the longitudinal direction of the device and comprising an inlet and an outlet in fluid communication with the interior of the barrel, said inlet and outlet being positioned spaced apart in the longitudinal direction of the barrel at a distance which is greater than the longitudinal extent of the front piston and which is shorter than the longitudinal extent of the rear piston.

After transfer of part of the fluid in the rear chamber past the front piston for the mixing purpose the front piston shall seal again against the barrel interior to keep the rinsing part of the rear chamber content separated from the mixture until the mixture has been ejected from the cartridge. The same sealing constraint for the front piston does not apply at the front bypass where the front piston has fulfilled its mission and the front piston can be brought into a permanently non-sealing state if desired. This allows for other front bypass arrangements over and beyond those described for the rear bypass, e.g. breaking or other destruction, possibly assisted by pre-designed weakening, of the front piston or, preferably, in order to avoid debris, tilting of the front piston for example by a stop peg projecting into the barrel from the wall of the barrel on one side, and the front bypass shall be understood to incorporate such alternatives. In such cases, in order to allow for complete ejection of the rinsing fluid unhindered by the remains of the front piston, spacer design alternatives, described below, able to penetrate into the front and/or rear pistons are preferred. The bypass arrangement alternatives described for the rear bypass arrangement can also be used for the front bypass although the need for prevention of backflow is less pronounced here.

In case of a bypass arrangement building on cooperation between a barrel bypass zone and the front and rear pistons it is clear that the longitudinal length of the barrel zone, i.e. the length of the bypass arrangement, and pistons' lengths need to be mutually adapted. Whereas the front piston length needs to be shorter than the length of the bypass arrangement (e.g. shorter than the distance between the bypass arrangement inlet and outlet), or the length of the internal protuberance in case of a bypass using piston deformation, the length of the rear piston is preferably longer than these zone lengths in order to provide a seal against the inner wall of the barrel and thereby preventing backflow.

The invention further relates to a method for manufacturing a two-chamber device arranged for serial ejection of at least two components, the method comprising a) providing a barrel with a front end arranged for component ejection and a rear end arranged for actuation, b) feeding into the barrel a movable front piston, defining a front chamber between the front piston and the barrel front, c) charging a first component into the front chamber, d) charging a second component into the barrel between the front piston and the rear end e) feeding into the barrel a movable rear piston, defining a rear chamber between the rear piston and the front piston, the rear chamber containing the second component, wherein a spacer is comprised in the device arranged to provide at least a first state allowing the front piston to be displaced forwards by action on the rear piston while a first part of the rear chamber second component is retained in the rear chamber.

It should be understood that the spacer can be introduced at the same time as the front piston, or before or at the same time as the rear piston. The spacer may be attached to one piston, be positioned between the pistons or be a part of one piston. The use of more than one spacer is also conceivable. Also, an optional lyophilisation step can be carried out at any suitable point of time after the first component has been introduced into the front chamber.

Furthermore the present invention relates to a method for serially ejecting at least two components from a two-chamber device, the device initially comprising a barrel having a longitudinal axis and a front end and a rear end, a first injectable component confined between the barrel front end and a movable front piston in the barrel, and a second injectable component confined between the front piston and a movable rear piston in the barrel, the method comprising a) moving the rear piston, at least part of the second component and the front piston together towards the front end to reduce the volume contained in the front chamber thereby ejecting at least a part of the first component from the barrel front end and b) moving the rear piston and the second component towards the front end to eject at least a part of the second component from the barrel front end past (or through) the front piston, the method comprising i) advancing before step a) the rear piston, while keeping the front piston substantially stationary, to decrease the rear chamber volume under simultaneous transfer of a mixing part of the rear chamber second component content to the front chamber and ii) maintaining before step b) a rinsing part of the rear chamber second component content in said rear chamber.

It is clear that in the intended operation of the cartridge described, a sequence of events takes place following movement of the rear piston. Thus, as the rear piston advances along the barrel, the rear bypass is opened, e.g. by moving the front piston into the barrel bypass zone, the mixing part of the fluid in the rear chamber is transferred past the front piston into the front chamber (3), the front piston is moved forwards with fluid retained in the rear chamber (5), the mixture is ejected from the cartridge; the front piston is moved into the front bypass arrangement and the rinsing fluid in the rear chamber is ejected past (or through) the front piston.

Various means can be used to control the above described sequence of events. For example pressure can be used as a sequencing controlling parameter, e.g. by opening the rear bypass at a certain pressure level, transfer of fluid past the front piston until the front piston is moved away at a certain pressure level for example if using a spring type spacer that overcomes the front piston friction at a certain force level, and/or using a pressure sensitive valve as the front bypass for determining when fluid from the rear chamber shall pass the front piston.

It is believed, however, that higher precision can be obtained by use of position as the sequencing controlling parameter, e.g. for opening the rear bypass at a certain location in the cartridge barrel, transfer of fluid past the front piston until the spacer abuts both front piston and rear piston with a predetermined spacing between them, and/or opening the front bypass when the front piston is in its foremost position where most of the mixture has been expelled.

Even if position is used as main sequencing controlling parameter pressure/force may still be involved as secondary parameter, for example by allowing build-up of sufficient pressure for e.g. operating a pressure sensitive valve or causing a pressure dependent spacer deformation, only after the front piston has been stopped by a retarding arrangement, for example a mechanical stop, such as the cartridge front end or another stop structure.

From the above it can be understood that transition from the first state to the second state of the spacer can take place in a variety of ways. The spacer need not change in shape during the transition but can be structurally intact. This can be obtained with a spacer acting differently under low and high forces respectively, as exemplified by pointed but dull structures able to push the front piston forward under low forces but which penetrate into one or both pistons under higher forces. The transition can also be controlled by the relative location between the spacer and barrel structures, as exemplified by a spacer in the form of a sleeve or cage attached to the rear piston and which follows its forward movement until a part of the sleeve in contact with the barrel shuts off an external bypass arrangement thereby ending fluid transfer through the bypass arrangement and then allowing rear chamber volume to shrink as the rinsing fluid is ejected by releasing the rear piston from the sleeve, which otherwise may prevent the rear piston from moving into its foremost position in the barrel. If a frictional engagement between sleeve and piston has been used, release can take place by increasing the force applied on the rear piston over a threshold, e.g. when the sleeve bottoms out at the cartridge front. If a mechanical interlock between sleeve and piston has been used release can take place by direct action on the parts of the interlock, which parts may be accessible from the rear end of the cartridge.

Preferably the spacer is able to change shape between the states, e.g. in order to obtain a more simple construction. The shape change need not take place between distinct configurations but can take place more or less continuously, as exemplified by a spring or other elastic element adapted to give a counterforce suitable for releasing the front piston for movement at a length compression corresponding to the desired separation between the pistons for the rinsing volume part of the rear chamber fluid.

For example in order to obtain better volume control the shape change can preferably take place between distinct state configurations. Although this can be reached by partly hydraulic means, such as a bag enclosing the rinsing amount of the rear chamber volume that can be crushed or punctured in the second state, it is preferred to use mechanically-based configurations, as these may provide the best storage and operation reliability. Such mechanically-based shape changes between distinct states can preferably comprise a self-amplifying process to secure passage of a non-stable intermediate phase. The process can be reversible such as in mono-stable or bi-stable structures, as exemplified by invertible domes, but irreversible change is sufficient for the present purposes, e.g. more or less permanent collapse of the spacer whereat a distinct second state configuration can be reached by use of for example a tipping deformation, facilitated by e.g. longitudinally elongated spacer elements with pre-weakening points or laterally asymmetrical support points.

The dual purpose of mixing and rinsing determines the proper division of the initial fluid content in the rear chamber. The necessary mixing volume is mainly determined by the total dose of the preparation to be delivered. The necessary rinsing volume is mainly determined by the dead volume in the cartridge front as well as any tube, needle or cannula attached to it. Typically the rinsing volume should be at least equal to the expected dead space volume, preferably at least 1.5 and most preferably at least 2 times the dead space volume. However since the volume of the dead space is not determined until the cartridge is being prepared for use and bears some relationship to the total dose of preparation it is preferred that the rinsing part of fluid is at least 10%, preferably at least 20% and most preferably at least 30% of the initial rear chamber volume. It is preferred that the mixing part of fluid is at least 10%, preferably at least 20% and most preferably at least 30% of the initial rear chamber volume.

The length of the rear chamber that is occupied by the spacer enables a predetermined volume of liquid to be retained in the rear chamber as the pistons are moved forward to mix the first and second component in the front chamber and subsequently eject the content of the front chamber. The spacer changes from a first length to a second length when a predetermined force greater than that needed to expel the reconstituted, dissolved or suspended first component from the front chamber is applied to the pistons, thereby expelling the retained volume of liquid ("the rinsing liquid") from the rear chamber into the front chamber and out through the outlet.

The invention also relates to the use of a device comprising a) a barrel, having a front with an outlet, or preparation for an outlet, b) a movable front piston in the barrel defining a front chamber between the front piston and the barrel front comprising a first component, c) a movable rear piston defining a rear chamber between the rear piston and the front piston comprising a second component, d) a rear bypass arrangement allowing fluid transfer from the rear chamber to the front chamber and e) a front bypass arrangement allowing fluid transfer past (or through) the front piston to the outlet, wherein a first part of the rear chamber second component is used for mixing with the first chamber first component and a second part of the rear chamber second component is used for rinsing dead spaces in front of the front piston.

DETAILED DESCRIPTION OF FIGURES

Figure 1:
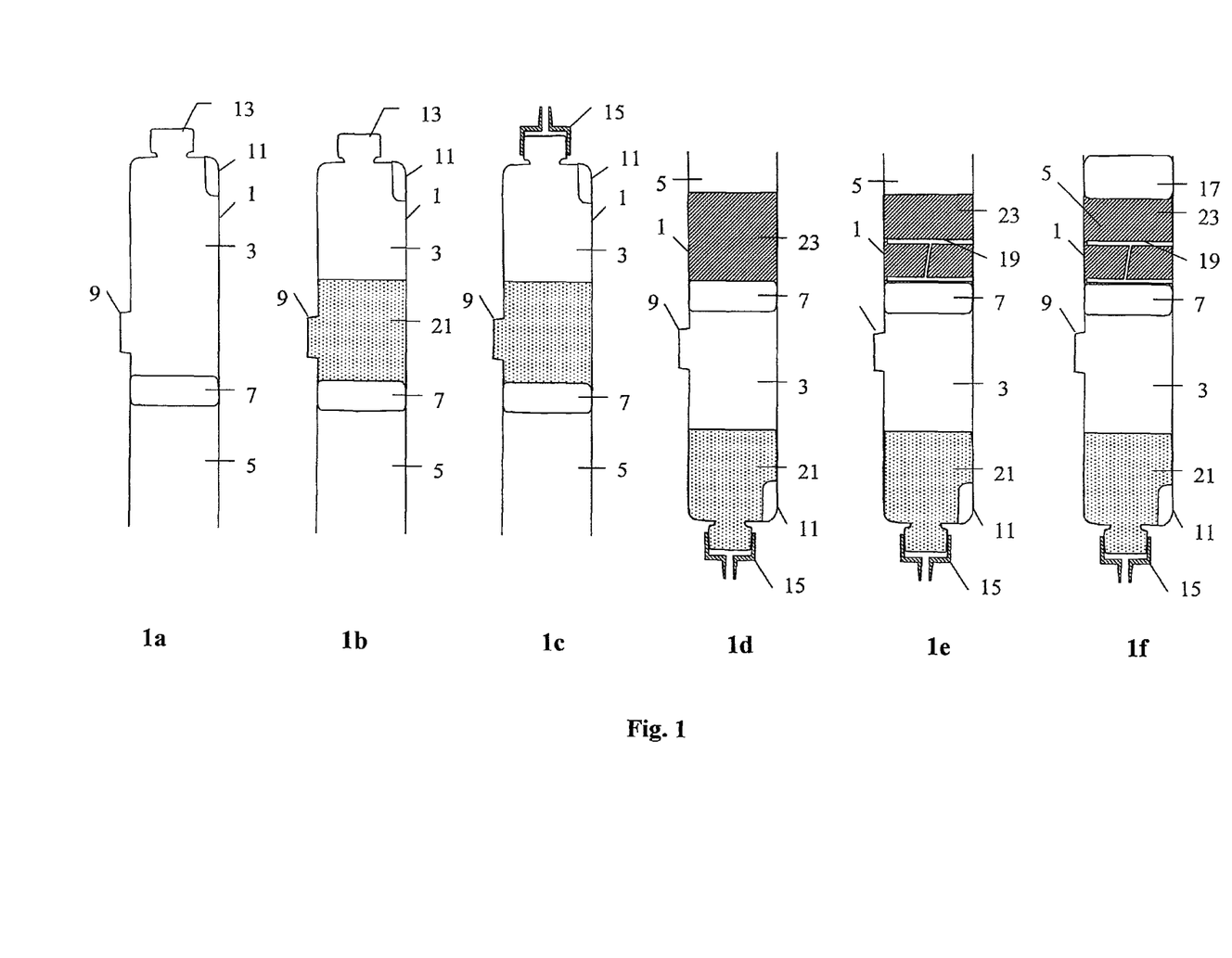
FIG. 1 illustrates one embodiment of the device according to the invention (FIG. 1f) and the steps of a method for manufacturing thereof (FIG. 1a-f).

FIG. 1f illustrates one embodiment of a two-chamber device in accordance with the present invention comprising a barrel having a front chamber (3) and a rear chamber (5) separated by a movable front piston (7), wherein the front chamber has a front outlet or a preparation for an outlet (13) and the rear chamber (5) is delimited by the rear face of the front piston (7) and the front face of a movable rear piston (17), said barrel also having a front bypass arrangement (11) for permitting fluid communication between the rear chamber (5) and the outlet (13) when said front piston (7) is positioned in its foremost position, and a rear bypass arrangement (9) for permitting fluid communication between the front chamber (3) and the rear chamber (5) when the front piston (7) is positioned in the rear bypass arrangement (9), wherein the rear chamber (5) contains an spacer (19) which provides at least two states, i) a first state allowing the front piston to be displaced forwards by action on the rear piston while a fluid volume is retained in the rear chamber, and ii) a second state allowing the rear chamber to volumetrically shrink while fluid is transferred past (or through) the front piston. The barrel also comprises an outlet seal (15).

FIGS. 1a-f illustrate one embodiment of a method in accordance with the present invention for manufacturing of a two-chamber device, in which embodiment the spacer is introduced into the barrel before the introduction of a rear piston, the method comprising the steps of:

A) providing an empty barrel (1) having a front bypass arrangement (11) and a rear bypass arrangement (9), oriented with its front end upwards and introducing into said barrel (1) a front piston (7) to a position below the rear bypass arrangement (9);

B) filling of a first component (21) into the front chamber (3) of said barrel (1) through the front end outlet (13), followed by applying a seal (15) to said outlet (13) and turning the barrel (1) upside down;

C) charging of a liquid component (23) into the rear chamber (5);

D) introducing into said barrel an spacer (19) which provides at least two states, i) a first state allowing the front piston to be displaced forwards by action on the rear piston while a fluid volume is retained in the rear chamber and ii) a second state allowing the rear chamber to volumetrically shrink while fluid is transferred past (or through) the front piston.

Figure 2:
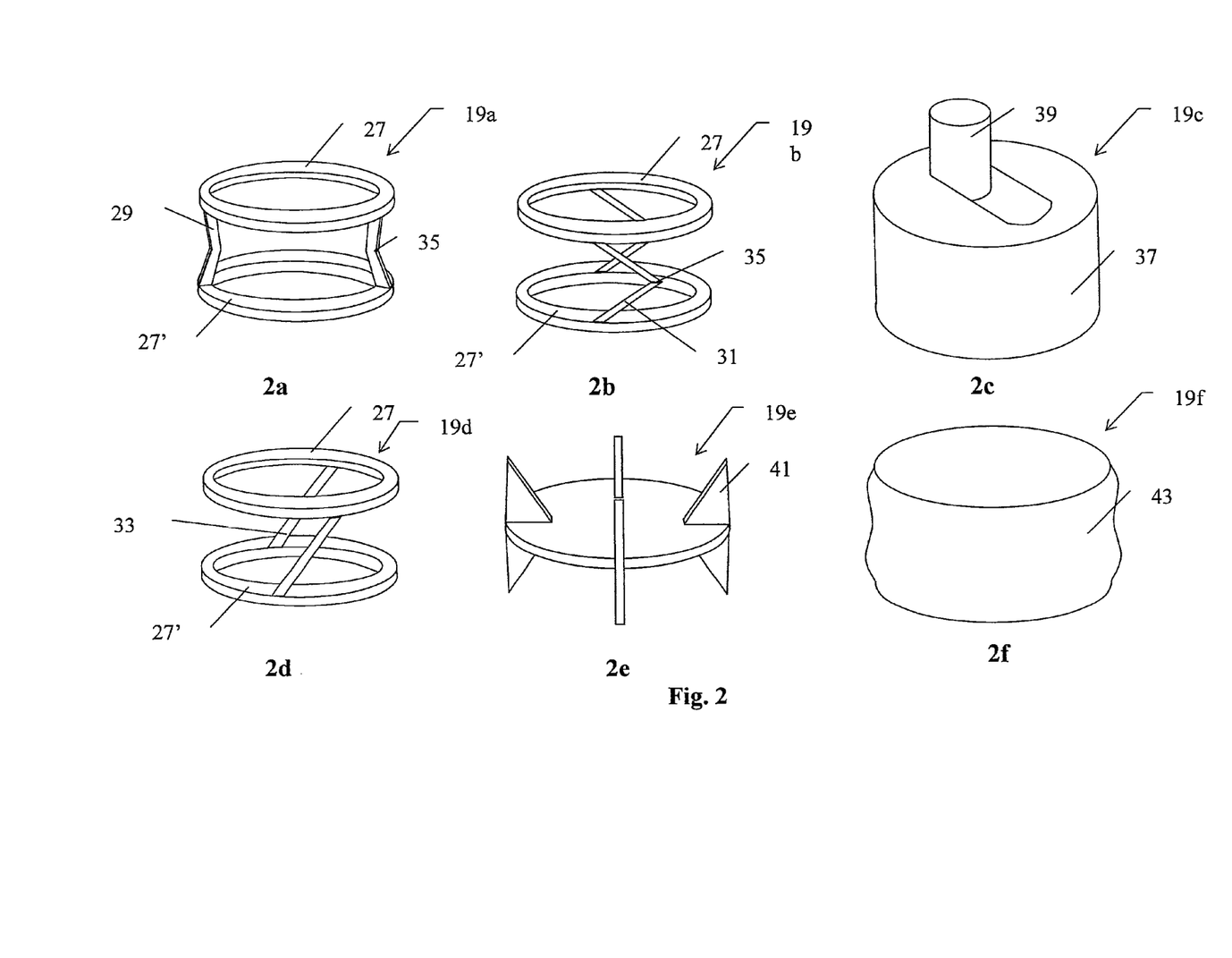
FIG. 2 illustrates examples of embodiments of the spacer of the device according to the invention.

FIG. 2 illustrates schematically various embodiments of spacers in accordance with the present invention drawn in an orientation assuming barrel longitudinal axis in an up/down direction.

In FIGS. 2a, 2b and 2d the spacer (19a, 19b, 19d) have contact surfaces in the form of rings 27 and 27' arranged respectively for contact with the front piston and the rear piston. Collapsible posts 29, 31 and 33 are arranged between the rings with an orientation angled with respect to the longitudinal axis, the posts being either straight 33 or having a change in angle 35, possibly with an additional collapse-controlling weakening at 35, somewhere along the posts. The angled arrangement assists in securing a self-amplifying process in which the spacer initially is able to transmit longitudinal forces in a first stable configuration but after an initial compression of the spacer, in its shown first state, compression is amplified by increasing bending angle moment relative axial forces into a second stable configuration of total post collapse, in a second state.

FIG. 2c illustrates a spacer (19c) wherein a piston 37, which can be the front and/or rear piston, comprises a separate or preferably integral pin 39 extending in the longitudinal direction and acting as the spacer. Although an upsetting type of collapse for the pin can be relied upon for transfer of the spacer from the first state to the second state it is preferred that the transfer is guided by an laterally asymmetrical support for the pin 39 to the piston 37 so as to bias lateral collapse into a pre-formed groove in the piston.

FIG. 2e illustrates a spacer (19e) having pointed but dull knifes 41. The knives are designed for, under low forces, causing displacement of the front piston together with the rear piston while maintaining a rinsing liquid amount in the rear chamber and are designed to be able, under forces which are higher than the low forces, to penetrate into the front and/or the rear piston for reduction of the rear chamber volume for expulsion of remaining liquid in the rear chamber. Control of this process can be assisted by pistons having a tough outer skin and softer inner material so as to facilitate penetration of the knives into the piston or pistons and preferably making the penetration irreversible.

FIG. 2f illustrates a spacer (19f) in which the spacer is designed as a bag 43 comprising the rinsing part of the rear chamber second component. If the content of the bag is liquid and the bag is sealed the bag will transfer forces from the rear piston to the front piston, corresponding to the spacer first state, until broken by e.g. being penetrated or by being subjected to pressure which causes it to burst, thereby transferring the bag into a second state in which its content can be used as a rinsing liquid part of the initial rear chamber second component.

Figure 3:
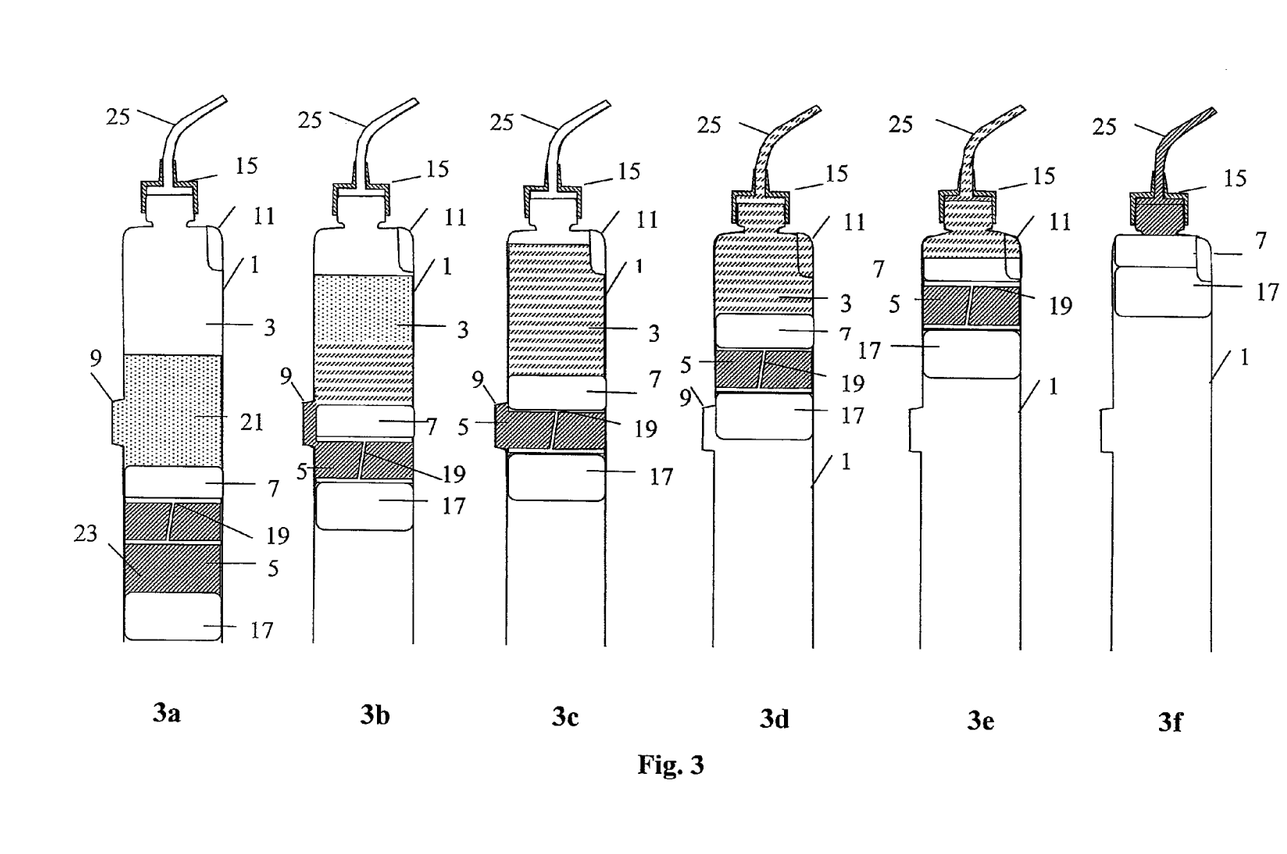
FIG. 3 illustrates one embodiment of the method for ejecting a liquid preparation and a rinsing liquid from a device according to the invention.

FIG. 3 illustrates one embodiment of a method for ejecting a liquid preparation and a rinsing liquid from a two-chamber device comprising the steps of:

A) reconstituting or dissolving or suspending first component (21) by allowing liquid component (23) to flow from rear chamber (5) to front chamber (3) as rear piston (17) is moved forward this movement causing front piston (7) to move into a position allowing liquid to flow through said bypass arrangement (9) for liquid passage into said front chamber (3) (FIG. 3b);

B) sealing of said bypass arrangement (9) by moving the front and rear pistons (7, 17) forward until the spacer (19) placed between them comes into contact with both front and rear pistons (7, 17), thereby retaining a liquid volume between front and rear pistons (7, 17) for later rinsing (FIG. 3c);

C) expelling said reconstituted, dissolved or suspended preparation through an outlet conduit (25) by moving the combined pistons (7, 17) with the spacer (19) forward until said front piston (7) takes its foremost position (FIGS. 3d and 3e); and D) applying a greater force to said rear piston (17) in order to reduce the length occupied by said spacer (19), and thereby expelling the rinsing liquid contained between said front and rear pistons (7, 17) through said outlet conduit (25) by the aid of a bypass arrangement (11) (FIG. 3f).

While bypass arrangements have been described as being simple ducts or protuberances, it is of course conceivable that any other form of bypass arrangement may be used.

The invention claimed is:

1. A device for the serial ejection of at least two fluid components comprising a) a barrel (1), having a longitudinal axis, having a front with an outlet or preparation for an outlet (13), b) a movable front piston (7) in the barrel defining a front chamber (3) between the front piston (7) and the barrel front, c) a movable rear piston (17) defining a rear chamber (5) between the rear piston (17) and the front piston (7), d) a rear bypass arrangement (9) allowing fluid transfer from the rear chamber (5) to the front chamber (3) and e) a front bypass arrangement (11) allowing fluid transfer past (or through) the front piston to the outlet (13), characterized in that the device further comprises a spacer (19-19f) being arranged to change shape between at least two states, i) a first state allowing the front piston (7) to be displaced forwards by action on the rear piston (17) while a fluid volume is retained in the rear chamber (5) and ii) a second state allowing the rear chamber to volumetrically shrink while fluid is transferred past (or through) the front piston thereby enabling the use of a liquid, initially provided in the rear chamber, for the dual purposes of mixing and rinsing.

2. A device in accordance with claim 1, characterized in that the spacer is formed as a crushable or puncturable bag enclosing a liquid, the bag with liquid occupying only a part of the rear chamber volume in the spacer first state.

3. A device in accordance with claim 1, characterized in that the spacer change shape takes place by a transition between distinct shape configurations.

4. A device in accordance with claim 3, characterized in that the transition takes place between mono-stable or bi-stable states.

5. A device in accordance with claim 3, characterized in that the transition takes place by a tipping action.

6. A device in accordance with claim 3, characterized in that the spacer comprises at least one pre-weakening arranged to assist the transition.

7. A device in accordance with claim 3, characterized in that the spacer comprises at least one support point, asymmetrical with respect to the barrel longitudinal direction, the support point being arranged to assist the transition.

8. A device in accordance with claim 3, characterized in that the spacer comprises at least one support post extending with an angle relative the barrel longitudinal axis, so as to give increasing bending moment on the post during spacer axial collapse.

9. A device in accordance with claim 1, characterized in that the spacer is part of the front piston and/or the rear piston.

10. A method for manufacturing a two-chamber device arranged for the serial ejection of at least two components, the method comprising a) providing a barrel (1) with a front end arranged for component ejection and a rear end arranged for pumping action, b) feeding into the barrel a movable front piston (7), defining a front chamber (3) between the front piston (7) and the barrel front, c) charging a first component (21) into the front chamber (3), d) charging a second component (23) into the barrel between the front piston (7) and the rear end e) feeding into the barrel a movable rear piston (17), defining a rear chamber (5) between the rear piston (17) and the front piston (7), the rear chamber (5) containing the second component (23), characterized by the step of including in the device a spacer (19-19f) arranged to provide at least a first state allowing the front piston (7) to be displaced forwards by action on the rear piston (17) while a first part of the rear chamber (5) second component is retained in the rear chamber, wherein the spacer is arranged to provide a second state allowing the rear chamber to decrease in volume under fluid transfer past (or through) the front piston, and wherein the spacer is arranged to change shape between the first state and the second state.

11. A method in accordance with claim 10, characterized in that at least 10% of the rear chamber second component is retained.

12. A method in accordance with claim 10, characterized in that the spacer is part of the front piston and/or the rear piston.

13. A method in accordance with claim 10, characterized in that the spacer is a separate element and that the including step comprises the step of feeding the element into the rear chamber.

14. A method in accordance with claim 10, characterized in that the step of feeding the element takes place prior to the step e).

15. A method in accordance with claim 10, characterized in that the step of feeding the element takes place prior to the step d).

16. A method of serially ejecting at least two components from a two-chamber device, the device initially comprising a barrel (1) having a longitudinal axis and a front end and a rear end, a first component (21) confined between the barrel front end and a movable front piston (7) in the barrel (1), and a second component (23) confined between the front piston (7) and a movable rear piston (17) in the barrel (1), the method comprising a) moving the rear piston (17), at least part of the second component (23) and the front piston (7) together towards the front end to eject at least a part of the first component (21) from the barrel front end and b) moving the rear piston (17) and the second component (23) towards the front end to eject at least a part of the second component (23) from the barrel front end past (or through) the front piston (7), characterized in i) advancing before step a) the rear piston (17), while keeping the front piston (7) substantially stationary, to decrease the rear chamber (5) volume under simultaneous transfer of a mixing part of the rear chamber (5) second component content to the front chamber (3) and ii) maintaining before step b) a rinsing part of the rear chamber (5) second component content, wherein the maintaining step ii) comprises using a spacer arranged to allow, in a first state, the front piston to be displaced forwards by action on the rear piston while the rinsing part is retained in the rear chamber.

17. A method in accordance with claim 16, characterized by during step i) mixing a solid part of the first component with the mixing part of the rear chamber second component.

18. A method in accordance with claim 17, characterized in that the mixing step comprises suspension, dissolution and/or reconstitution of the solid part.

19. A method in accordance with claim 16, characterized by during step b) flushing dead spaces of a conduit attached to the barrel front end by use of the rinsing part.

20. A method in accordance with claim 19, characterized in that the rinsing part has a volume at least equal to the dead space volume.

21. A method in accordance with claim 16, characterized in that the spacer is arranged to allow, in a second state, the rear chamber to decrease in volume during step b).

22. A method in accordance with claim 21, characterized in that it comprises a transfer step during which the spacer is brought from the first state to the second state.

23. A method in accordance with claim 22, characterized in that the transfer step comprises increasing pressure over the spacer in the longitudinal axis direction.

24. A method in accordance with claim 22, characterized in that the transfer step comprises collapse of the spacer in the longitudinal axis direction.

25. A method in accordance with claim 22, characterized in that the transfer step comprises penetration in the longitudinal axis direction of spacer parts into the front piston and/or the rear piston.

* * * * *